US008569272B2

(12) United States Patent
Lyons et al.

(10) Patent No.: US 8,569,272 B2
(45) Date of Patent: Oct. 29, 2013

(54) METHODS FOR TREATING A POSTERIOR SEGMENT OF AN EYE

(75) Inventors: Robert T. Lyons, Laguna Hills, CA (US); James N. Chang, Newport Beach, CA (US); John T. Trogden, Anaheim, CA (US); Scott M. Whitcup, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 304 days.

(21) Appl. No.: 12/172,194

(22) Filed: Jul. 11, 2008

(65) Prior Publication Data

US 2008/0269181 A1    Oct. 30, 2008

Related U.S. Application Data

(62) Division of application No. 10/966,764, filed on Oct. 14, 2004.

(60) Provisional application No. 60/519,237, filed on Nov. 12, 2003, provisional application No. 60/530,062, filed on Dec. 16, 2003.

(51) Int. Cl.
*A01N 45/00* (2006.01)
*A61F 2/00* (2006.01)
*A61K 9/14* (2006.01)
*A61K 33/32* (2006.01)

(52) U.S. Cl.
USPC ............ 514/169; 424/427; 424/489; 424/643

(58) Field of Classification Search
USPC .......................... 514/169; 424/427, 489, 643
See application file for complete search history.

(56) References Cited

U.S. PATENT DOCUMENTS

| | | | |
|---|---|---|---|
| 4,383,992 A | 5/1983 | Lipari | 424/438 |
| 4,713,446 A * | 12/1987 | DeVore et al. | 530/356 |
| 4,853,224 A | 8/1989 | Wong | 424/427 |
| 4,920,104 A | 4/1990 | DeVore et al. | |
| 4,941,874 A | 7/1990 | Sandow et al. | 604/60 |
| 4,997,652 A | 3/1991 | Wong | 424/428 |
| 5,098,443 A | 3/1992 | Parel et al. | 623/4 |
| 5,164,188 A | 11/1992 | Wong | 424/428 |
| 5,209,926 A | 5/1993 | Babcock | 424/78.04 |
| 5,256,408 A | 10/1993 | Babcock et al. | 424/78.04 |
| 5,378,475 A | 1/1995 | Smith et al. | 424/473 |
| 5,443,505 A | 8/1995 | Wong et al. | 623/4 |
| 5,516,522 A | 5/1996 | Peyman et al. | 424/426 |
| 5,576,311 A | 11/1996 | Guy | 514/179 |
| 5,770,589 A | 6/1998 | Billson | 514/174 |
| 6,107,347 A | 8/2000 | Francese et al. | 514/772 |
| 6,217,895 B1 | 4/2001 | Guo et al. | 424/427 |
| 6,271,216 B1 | 8/2001 | Mello et al. | 514/78.04 |
| 6,395,294 B1 | 5/2002 | Peyman | 424/427 |
| 6,548,078 B2 | 4/2003 | Guo et al. | 424/423 |
| 2003/0060763 A1 | 3/2003 | Penfold et al. | |
| 2003/0171320 A1 | 9/2003 | Guyer | |
| 2004/0077562 A1 | 4/2004 | Chandavarkar et al. | 514/36 |
| 2005/0065137 A1 | 3/2005 | Jani et al. | 514/171 |
| 2005/0101582 A1 | 5/2005 | Lyons et al. | 514/179 |
| 2005/0181017 A1 | 8/2005 | Hughes et al. | 424/427 |
| 2005/0244468 A1 | 11/2005 | Huang et al. | 424/427 |
| 2005/0250737 A1 | 11/2005 | Hughes et al. | 514/58 |
| 2006/0009498 A1 | 1/2006 | Whitcup | 514/357 |
| 2006/0173060 A1 | 8/2006 | Chang | 514/389 |

FOREIGN PATENT DOCUMENTS

| | | |
|---|---|---|
| EP | 0197718 A2 | 3/1986 |
| EP | 244178 A2 | 4/1987 |
| WO | WO0002564 | 1/2000 |
| WO | WO 02/089815 A2 | 11/2002 |
| WO | WO 02/100437 A1 * | 12/2002 |
| WO | WO 2004/069280 A1 | 8/2004 |
| WO | WO 2004/087043 A2 | 10/2004 |

OTHER PUBLICATIONS

Geroski et al., Drug Delivery for Posterior Segment Eye Disease, Apr. 2000, Investigative Ophthalmology & Visual Science, vol. 41, No. 5, pp. 961-964.*
Pulido et al., The use of 31-gauge needles and syringes for intraocular injections, 2006, Eye, vol. 21, pp. 829-830.*
Calvo et al., Comparative in vitro Evaluation of Several Colloidal Systems, Nanoparticles, Nanocapsules, and Nanoemulsions, as Ocular Drug Carriers, 1996, Journal of Pharmaceutical Sciences, vol. 85, No. 5, pp. 530-536.*
Fokjaet et al., Pharmaceutical Formulation Development of Peptides and Proteins, Taylor & Francis Limited, 2000, p. 131.*
Beer et al., Intraocular concentration and pharmacokinetics of trimcinolone acetonide after a single intravitreal injection, Ophthalmology, Apr. 2003, Edition 110, vol. 4, pp. 681-686.*
Antcliff R., et al Marshall J., *The pathogenesis of edema in diabetic maculopathy*, Semin Ophthalmol 1999; 14:223-232.

(Continued)

*Primary Examiner* — Maria Leavitt
*Assistant Examiner* — Kyung Sook Chang
(74) *Attorney, Agent, or Firm* — Laura L. Wine; Allergan, Inc.

(57) ABSTRACT

Compositions, and methods of using such compositions, useful for injection into the posterior segments of human or animal eyes are provided. Such compositions include corticosteroid component-containing particles present in a therapeutically effective amount, a viscosity inducing component, and an aqueous carrier component. The compositions have viscosities of at least about 10 cps or about 100 cps at a shear rate of 0.1/second. In a preferred embodiment, the viscosity is in the range of from about 140,000 cps to about 300,000 cps. The compositions advantageously suspend the particles for prolonged periods of time.

18 Claims, No Drawings

(56) References Cited

OTHER PUBLICATIONS

Armaly M., *Statistical attributes of the steroid hypertensive response in the clinically normal eye*, Invest Ophthalmol Vis Sci 1965; 4:187-197.

Audren, F. et al., *Pharmacokinetic-Pharmacodynamic modeling of the effect of Triamcinolone Acetonide on Central Macular Thickness in Patients with Diabetic Macular Edema*, Inv Ophth & Vis Sci, 45(10); 3435-3441: Oct. 2004.

Becker B,. *Intraocular pressure response to topical corticosteroid*, Invest Ophthalmol Vis Sci 1965; 4:198-205.

Beer P. et al., *Intraocular concentration and pharmacokinetics of triamcinolone acetonide after a single intravitreal injection*, Opthal 110(4); 681-686: Apr. 2003.

Butcher J. et al., *Bilateral cataracts and glaucoma induced by long term use of steroid eye drops*. BMJ 1994; 309-343.

Challa J. et al., *Exudative macular degeneration and intravitreal triamcinolone: 18 month follow up*, Aust NZ J Ophthalmol 1998; 26:277-281.

Chang H. et al., *Development of a topical suspension containing three active ingredient*, Drug Dev and Ind Pharm, 28(1), 29-39 (2002).

Cheng, Cheng-Kuo et al., *Intravitreal Sustained-Release Dexamethasone Device in the Treatment of Experimental Uveitis*, Investigative Ophthalmology & Visual Science, Feb. 1995, vol. 36, No. 2, pp. 442-453.

Danis R. et al., *Intravitreal triamcinolone acetonide in exudative age-related macular degeneration*, Retina 2000; 20:244-250.

Dea I. et al., *Hyaluronic acid: a novel, double helical molecule*, Science, Feb. 9, 1973;179(73):560-2.

Edelman et al., *Corticosteroids inhibit VEGF-induced vascular leakage in a rabbit model of blood-retinal and blood-aqueous barrier breakdown*, Exp Eye Res Feb. 2005;80(2):249-58.

Einmahl S. et al, *Evaluation of a novel biomaterial in the suprachoroidal space of the rabbit eye*, Invest Ophthal & Vis Sci 43(5); 1533-1539 (2002).

Einmahl S. et al, *Therapeutic applications of viscous and injectable poly(ortho esters)*, Adv Drug Del Rev 53 (2001) 45-73.

Enyedi, Laura et al., *An Intravitreal Device Providing Sustained Release of Cyclosporine and Dexamethasone*, Current Eye Research (1995) pp. 549-557.

Hainsworth, Dean P. et al., *Sustained Release Intravitreal Dexamethasone*, Journal of Ocular Pharmacology and Therapeutics, (1996) vol. 12, No. 1, pp. 57-63.

Helliwell P., *Use of an objective measure of articular stiffness to record changes in finger joints after intra-articular injection of corticosteroid*, Ann Rheum Dis 1997;56:71-73.

Inoue M. et al., *Vitreous concentrations of triamcinolone acetonide in human eyes after intravitreal or subtenon injection*, Am J Opth 138(6); 1046-1048: 2004.

Jonas J. et al., *Intraocular injection of crystalline cortisone as adjunctive treatment of diabetic macular edema*, Am J Ophthalmol 2001; 132:425-427.

Jonas J. et al., *Intravitreal injection of crystalline cortisone as adjunctive treatment of proliferative vitreoretinopathy*, Br J Ophthalmol 2000; 84:1064-1067.

Jonas J. et al., *Intravitreal injection of triamcinolone for diffuse diabetic macular edema*, Arch Ophthalmol 2003; 121:57-61.

Kochinke, F. et al., Biodegradable Drug Delivery System for Uveitis Treatment, Investigative Ophthalmology & Visual Science, Feb. 15, 1996, vol. 37. No. 3, 186-B98.

Martidis A. et al., *Intravitreal triamcinolone for refractory diabetic macular edema*, Ophthalmology 2002; 109:920-927.

McCarty D., et al., *Inflammatory reaction after intrasynovial injection of microcrystalline adrenocorticosteroid esters*, Arthritis and Rheumatism, 7(4); 359-367 (1964).

McCuen B. et al., *The lack of toxicity of intravitreally administered triamcinolone acetonide*, Am J Ophthalmol 1981; 91:785-788.

Nauck M. et al., *Corticosteroids inhibit the expression of the vascular endothelial growth factor gene in human vascular smooth muscle cells*, Euro J Pharmacol 1998; 341:309-315.

Nauck M. et al., *Induction of vascular endothelial growth factor by platelet-activating factor and platelet-derived growth factor is downregulated by corticosteroids*, Am J Resp Cell Mol Biol 1997; 16:398-406.

Nishimura A. et al., *Isolating Triamcinolone acetonide particles for intravitreal use with a porous membrane filter*, Retina, vol. 23(6); 777-779 (2003).

Pe'er J. et al., *Vascular endothelial growth factor upregulation in human central retinal vein occlusion*, Ophthalmology 1998; 105:412-416.

Penfold P. et al., *Exudative macular degeneration and intravitreal triamcinolone: A pilot study*, Aust NZ J Ophthalmol 1995; 23:293-298.

Roth D. et al., *Noninfectious endophthalmitis associated with intravitreal triamcinolone injection*, Arch Opthalmol 2003; 121: 1279-1282.

Schindler R. et al., *The clearance of intravitreal triamcinolone acetonide*, Am J Ophthalmol 1982; 93:415-417.

Scholes G. et al., *Clearance of triamcinolone from vitreous*, Arch Ophthalmol 1985; 103:1567-1569.

Sutter F. et al., *Pseudo-endophthalmitis after intravitreal injection of triamcinolone*, Br J Ophthalmol 2003; 87:972-974.

Roth et al, "Noninfectious Endophthalmitis Associated With Intravitreal Triamcinolone Injection", Arch. Ophthalmol., 121, 1279-1282, (2003).

Westfall et al, "Acute Endophthalmitis Incidence", Arch Ophthalmol., 123, 1075-1966 (2005).

Wang et al, "Sterile Endophthalmitis Following Intravitreal Injection of Triamcinolone Acetonide", Ocul. Immunol. Inflamm., 13, 295-300, (2005).

Maia et al, "Effects of intravitreal triamcinolone acetonide injection with and without preservative", Br. J. Ophthalmol. 91-1122-1134, (Mar. 2007).

\* cited by examiner

METHODS FOR TREATING A POSTERIOR SEGMENT OF AN EYE

RELATED APPLICATIONS

This application is a divisional of application Ser. No. 10/966,764 filed Oct. 14, 2004 which application claims the benefit of U.S. Provisional Patent Application Ser. No. 60/519,237, filed Nov. 12, 2003 and U.S. Provisional Patent Application Ser. No. 60/530,062, filed Dec. 16, 2003, the entire content of which prior applications are hereby incorporated by reference in their entireties.

This invention relates to compositions and methods for treating posterior segments of eyes of humans or animals. More particularly, the invention relates to compositions including corticosteroid components which can be effectively injected into posterior segments of such eyes and to methods of using such compositions to provide desired therapeutic effects.

Among the therapies currently being practiced to treat ocular posterior segment disorders, such as uveitis, macular degeneration, macular edema and the like, is intravitreal injection of a corticosteroid, such as triamcinolone acetonide (TA). See, for example, Billson et al U.S. Pat. No. 5,770,589, the disclosure of which is incorporated in its entirety herein by reference. One medication commonly employed for this ophthalmic therapy is Kenalog®40. Each milliliter (ml) of the Kenalog®40 composition includes 40 milligrams (mg) of TA, sodium chloride as a tonicity agent, 10 mg of benzyl alcohol as a preservative, and 7.5 mg of carboxymethylcellulose and 0.4 mg of polysorbate 80 as resuspension aids. Although widely used by ophthalmologists, this commercially available formulation suffers from several important limitations.

For example, the presence of benzyl alcohol preservative and polysorbate 80 surfactant tends to lead to unnecessary and/or undue cell damage or other toxicities in sensitive ocular tissues. Even though some clinicians routinely "wash" the TA precipitate several times with saline to reduce the concentration of these undesirable materials, such washing is inconvenient, time consuming, and most importantly, increases the probability of microbial or endotoxin contamination that could lead to intraocular infection and inflammation.

Moreover, the TA in the Kenalog®40 tends to rapidly separate and precipitate from the remainder of the composition. For example, this composition, if left standing for 1 to 2 hours, results in a substantial separation of a TA precipitate from the remainder of the composition. Thus, if the composition is to be injected into the eye, it must be vigorously shaken and used promptly after being so shaken in order to provide a substantially uniform suspension in the eye. In addition, resuspension processing requires the use of the resuspension aids noted above, at least one of which is less than totally desirable for sensitive ocular tissues.

There is a need for new compositions for injection into the posterior segments of eyes of humans or animals and methods for providing desired therapeutic effects in the posterior segments of eyes of humans or animals.

SUMMARY OF THE INVENTION

New compositions and methods for treating posterior segments of eyes of humans or animals have been discovered. The present compositions are highly suitable for intravitreal administration into the posterior segments of eyes without requiring any "washing step", while providing for reduced ocular, for example, retinal, damage when used in an eye. The present compositions are advantageously substantially free of added preservative components, for example, contain no benzyl alcohol preservative. In addition, the present compositions advantageously require no resuspension aid or aids. Overall, the present compositions are easily and effectively injectable into the posterior segment of an eye of a human or animal and can be maintained as a substantially uniform suspension for long periods of time, for example, at least about one week or more, without resuspension processing, for example, without requiring shaking or other agitating of the composition to obtain substantial suspension uniformity. In short, the present compositions and methods provide substantial enhancements and advantages, for example, relative to the prior art Kenalog®40 composition and methods of using such prior art composition, in the posterior segments of human or animal eyes.

In one broad aspect of the present invention, compositions useful for injection into a posterior segment of an eye of a human or animal are provided. Such compositions comprise a corticosteroid component, a viscosity inducing component, and an aqueous carrier component. The corticosteroid component is present in a therapeutically effective amount. The corticosteroid component is present in the compositions in a plurality of particles.

The present compositions may include a corticosteroid component in an amount of up to about 25% (w/v) or more of the composition. In one very useful embodiment, the corticosteroid component is present in an amount of at least about 80 mg/ml of composition. Preferably, the corticosteroid component is present in an amount in a range of about 1% to about 10% or about 20% (w/v) of the composition.

In one very useful embodiment, the corticosteroid component comprises triamcinolone acetonide.

The viscosity inducing component is present in an amount effective in increasing the viscosity of the composition.

Any suitable, preferably ophthalmically acceptable, viscosity inducing component may be employed in accordance with the present invention. Many such viscosity inducing components have been proposed and/or used in ophthalmic compositions used on or in the eye. Advantageously, the viscosity inducing component is present in an amount in a range of about 0.5% to about 20% (w/v) of the composition. In one particularly useful embodiment, the viscosity inducing component is a hyaluronic acid polymer component, such as sodium hyaluronate.

In one embodiment, the present compositions have a viscosity of at least about 10 cps or at least about 100 cps, preferably at least about 1,000 cps, more preferably at least about 10,000 cps and still more preferably at least about 70,000 cps, for example, up to about 250,000 cps, or about 300,000 cps, at a shear rate of 0.1/second. The present compositions are structured or have make-ups so as to be effectively, for example, manually, injected into a posterior segment of an eye of a human or animal, preferably through a 27 gauge needle, more preferably through a 29 or 30 gauge needle.

Without wishing to limit the invention to any particular theory of operation, it is believed that the use of relatively high viscosity compositions, as described herein, provides for effective, and preferably substantially uniform, suspension of the steroid component particles while, at the same time, being injectable into injectable into the posterior segment of an eye through conventionally, or even smaller than conventionally, used needles.

In one embodiment of the invention, the corticosteroid component is present in a plurality of particles which are substantially uniformly suspended in the composition and remain substantially uniformly suspended in the composition for at least about 1 week, preferably at least about 2 weeks or at least about 1 month, and still more preferably at least about 6 months or at least about 1 year or at least about 2 years, without requiring resuspension processing, that is, without requiring being shaken or otherwise agitated to maintain the corticosteroid component particles substantially uniformly suspended in the composition.

Compositions having such substantially uniform suspension of corticosteroid component particles provide substantial advantages relative to the prior art. In particular, the present compositions may be manufactured, shipped and stored for substantial periods of time without the corticosteroid component particles precipitating from the remainder of the composition. Having the corticosteroid component particles maintained substantially uniformly suspended in the composition allows the composition to be quickly and effectively used to provide treatment to the posterior segment of an eye of a human or animal without concern for having to resuspend such particles.

The aqueous carrier component is advantageously ophthalmically acceptable and may include one or more conventional expedients useful in ophthalmic compositions.

For example, the carrier component may include an effective amount of at least one of a preservative component, a tonicity component and a buffer component. In one advantageous embodiment, the present compositions include no added preservative component. This feature reduces or minimizes or even substantially eliminates adverse reactions in the eye which may be caused by or linked to the presence of a preservative component.

Although a resuspension component may be employed in accordance with the present invention, in many instances, because of the ability of the present composition to remain a substantially uniform suspension for a long period of time without requiring resuspension processing, the compositions advantageously contain no added resuspension components.

Methods of treating posterior segments of the eyes of humans or animals are also disclosed and are included within the scope of the present invention. In general, such methods comprise administering, e.g. injecting a corticosteroid component-containing composition, for example, a composition in accordance with the present intention, to a posterior segment of an eye of a human or animal. Such administering is effective in providing a desired therapeutic effect. The administering step advantageously comprises at least one of intravitreal injecting, subconjunctival injecting, sub-tenon injecting, retrobulbar injecting, suprachoroidal injecting and the like.

Each and every feature described herein, and each and every combination of two or more of such features, is included within the scope of the present invention provided that the features included in such a combination are not mutually inconsistent.

These and other aspects and advantages of the present invention are apparent in the following detailed description, examples and claims.

DETAILED DESCRIPTION

The present invention involves compositions useful for placement, preferably by injection, into a posterior segment of an eye of a human or animal. Such compositions in the posterior, e.g., vitreous, of the eye are therapeutically effective against one or more conditions and/or diseases of the posterior of the eye, and/or one or more symptoms of such conditions and/or diseases of the posterior of the eye.

In general, the present compositions comprise a corticosteroid component; a viscosity inducing component; and an aqueous carrier component. The compositions are advantageously ophthalmically acceptable.

One of the important advantages of the present compositions is that they are more compatible with or friendly to the tissues in the posterior segment of the eye, for example, the retina of the eye, relative to compositions previously proposed for intravitreal injection into a posterior segment of an eye, for example, a composition sold under the trademark Kenalog®40. In particular, the present compositions advantageously are substantially free of added preservative components or include effective preservative components which are more compatible with or friendly to the posterior segment, e.g., retina, of the eye relative to benzyl alcohol, which is included in the Kenalog®-40 composition as a preservative.

In addition, the present compositions preferably include no added resuspension component or a resuspension component which is more compatible with or friendly to the posterior segment, e.g., retina, of the eye relative to polysorbate-80, which is included in the Kenalog®-40 composition. Many of the other features of the present compositions, as described elsewhere herein, also render the present compositions more compatible with or friendly to the posterior segments of the eyes into which the compositions are placed relative to prior art compositions, such as Kenalog®-40.

As noted above, the present compositions include a corticosteroid component. Such corticosteroid component is present in the compositions in a therapeutically effective amount, that is in an amount effective in providing a desired therapeutic effect in the eye into which the composition is placed. The corticosteroid component is present in the composition in a plurality of particles.

Any suitable corticosteroid component may be employed in according to the present invention. Such corticosteroid component advantageously has a limited solubility in water, for example, at 25° C. For example, the corticosteroid component preferably has a solubility in water at 25° C. of less than 10 mg/ml. Of course, the corticosteroid component should be ophthalmically acceptable, that is, should have substantially no significant or undue detrimental effect of the eye structures or tissues. One particularly useful characteristic of the presently useful corticosteroid components is the ability of such component to reduce inflammation in the posterior segment of the eye into which the composition is placed caused by the result of one or more diseases and/or conditions in the posterior segment of the eye.

Examples of useful corticosteroid components include, without limitation, is cortisone, prednesolone, triamcinolone, triamcinolone acetonide, fluorometholone, dexamethosone, medrysone, loteprednol, derivatives thereof and mixtures thereof. As used herein, the term "derivative" refers to any substance which is sufficiently structurally similar to the material of which it is identified as a derivative so as to have substantially similar functionality or activity, for example, therapeutic effectiveness, as the material when the substance is used in place of the material.

In one very useful embodiment, the corticosteroid component comprises triamcinolone acetonide.

The corticosteroid component advantageously is present in an amount of at least about 10 mg per ml of the composition. One important advantage of the present invention is the effective ability of the present compositions to include relatively large amounts or concentrations of the corticosteroid component. Thus, the corticosteroid component may be present in the present compositions in an amount in the range of about 1% or less to about 5% or about 10% or about 20% or about 30% or more (w/v) of the composition. Providing relatively high concentrations or amounts of corticosteroid component in the present compositions is beneficial in that reduced amounts of the composition may be required to be placed or injected into the posterior segment of the eye in order to provide the same amount or more corticosteroid component in the posterior segment of the eye relative to compositions, such as Kenalog®-40, which include less than 4% (w/v) of the corticosteroid component. Thus, in one very useful embodiment, the present compositions include more than about 4% (w/v), for example at least about 5% (w/v), to about 10% (w/v) or about 20% (w/v) or about 30% (w/v) of the corticosteroid component.

The viscosity inducing component is present in an effective amount in increasing, advantageously substantially increasing, the viscosity of the composition. Without wishing to limit the invention to any particular theory of operation, it is believed that increasing the viscosity of the compositions to values well in excess of the viscosity of water, for example, at least about 100 cps at a shear rate of 0.1/second, compositions which are highly effective for placement, e.g., injection, into the posterior segment of an eye of a human or animal are obtained. Along with the advantageous placement or injectability of the present compositions into the posterior segment, the relatively high viscosity of the present compositions are believed to enhance the ability of the present compositions to maintain the corticosteroid component particles in substantially uniform suspension in the compositions for prolonged periods of time, for example, for at least about one week, without requiring resuspension processing. The relatively high viscosity of the present compositions may also have an additional benefit of at least assisting the compositions to have the ability to have an increased amount or concentration of the corticosteroid component, as discussed elsewhere herein, for example, while maintaining such corticosteroid component in substantially uniform suspension for prolonged periods of time.

Advantageously, the present compositions have viscosities of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. The present compositions not only have the relatively high viscosity as noted above but also have the ability or are structured or made up so as to be effectively placeable, e.g., injectable, into a posterior segment of an eye of a human or animal, preferably through a 27 gauge needle, or even through a 30 gauge needle.

The presently useful viscosity inducing components preferably are shear thinning components in that as the present composition containing such a shear thinning viscosity inducing component is passed or injected into the posterior segment of an eye, for example, through a narrow space, such as 27 gauge needle, under high shear conditions the viscosity of the composition is substantially reduced during such passage. After such passage, the composition regains substantially its pre-injection viscosity so as to maintain the corticosteroid component particles in suspension in the eye.

Any suitable viscosity inducing component, for example, ophthalmically acceptable viscosity inducing component, may be employed in accordance with the present invention. Many such viscosity inducing components have been proposed and/or used in ophthalmic compositions used on or in the eye. The viscosity inducing component is present in an amount effective in providing the desired viscosity to the composition. Advantageously, the viscosity inducing component is present in an amount in a range of about 0.5% or about 1.0% to about 5% or about 10% or about 20% (w/v) of the composition. The specific amount of the viscosity inducing component employed depends upon a number of factors including, for example and without limitation, the specific viscosity inducing component being employed, the molecular weight of the viscosity inducing component being employed, the viscosity desired for the present composition being produced and/or used and the like factors. The viscosity inducing component is chosen to provide at least one advantage, and preferably multiple advantages, to the present compositions, for example, in terms of each of injectability into the posterior segment of the eye, viscosity, sustainability of the corticosteroid component particles in suspension, for example, in substantially uniform suspension, for a prolonged period of time without resuspension processing, compatibility with the tissues in the posterior segment of the eye into which the composition is to be placed and the like advantages. More preferably, the selected viscosity inducing component is effective to provide two or more of the above-noted benefits, and still more preferably to provide all of the above-noted benefits.

The viscosity inducing component preferably comprises a polymeric component and/or at least one viscoelastic agent, such as those materials which are useful in ophthalmic surgical procedures.

Examples of useful viscosity inducing components include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

The molecular weight of the presently useful viscosity inducing components may be in a range of about 10,000 Daltons or less to about 2 million Daltons or more. In one particularly useful embodiment, the molecular weight of the viscosity inducing component is in a range of about 100,000 Daltons or about 200,000 Daltons to about 1 million Daltons or about 1.5 million Daltons. Again, the molecular weight of the viscosity inducing component useful in accordance with the present invention, may vary over a substantial range based on the type of viscosity inducing component employed, and the desired final viscosity of the present composition in question, as well as, possibly one or more other factors.

In one very useful embodiment, a viscosity inducing component is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component preferably is in a range of about 50,000 Daltons or about 100,000 Daltons to about 1.3 million Daltons or about 2 million Daltons.

In one embodiment, the present compositions include a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation rate to the extent that often no resuspension processing is necessary over the estimated shelf life, for example, at least about 2 years, of the composition. Such a composition may be marketed in pre-filled syringes since the gel cannot be easily removed by a needle and syringe from a bulk container.

The aqueous carrier component is advantageously ophthalmically acceptable and may include one or more conventional excipients useful in ophthalmic compositions.

The present compositions preferably include a major amount of liquid water. The present compositions may be, and are preferably, sterile, for example, prior to being used in the eye.

The present compositions preferably include at least one buffer component in an amount effective to control the pH of the composition and/or at least one tonicity component in an amount effective to control the tonicity or osmolality of the compositions. More preferably, the present compositions include both a buffer component and a tonicity component.

The buffer component and tonicity component may be chosen from those which are conventional and well known in the ophthalmic art.

Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, any other suitable ophthalmically acceptably tonicity component and mixtures thereof.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The present compositions may include one or more other components in amounts effective to provide one or more useful properties and/or benefits to the present compositions. For example, although the present compositions may be substantially free of added preservative components, in other embodiments, the present compositions include effective amounts of preservative components, preferably such components which are more compatible with or friendly to the tissue in the posterior segment of the eye into which the composition is placed than benzyl alcohol. Examples of such preservative components include, without limitation, benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

In addition, the present composition may include an effective amount of resuspension component effective to facilitate the suspension or resuspension of the corticosteroid component particles in the present compositions. As noted above, in certain embodiments, the present compositions are free of added resuspension components. In other embodiments of the present compositions effective amounts of resuspension components are employed, for example, to provide an added degree of insurance that the corticosteroid component particles remain in suspension, as desired and/or can be relatively easily resuspended in the present compositions, such resuspension be desired. Advantageously, the resuspension component employed in accordance with the present invention, if any, is chosen to be more compatible with or friendly to the tissue in the posterior segment of the eye into which the composition is placed than polysorbate 80.

Any suitable resuspension component may be employed in accordance with the present invention. Examples of such resuspension components include, without limitation, surfactants such as poloxanes, for example, sold under the trademark Pluronic®; tyloxapol; sarcosinates; polyethoxylated castor oils, other surfactants and the like and mixtures thereof.

One very useful class of resuspension components are those selected from vitamin derivatives. Although such materials have been previously suggested for use as surfactants in ophthalmic compositions, they have been found to be effective in the present compositions as resuspension components. Examples of useful vitamin derivatives include, without limitation, Vitamin E tocopheryl polyethylene glycol succinates, such as Vitamin E tocopheryl polyethylene glycol 1000 succinate (Vitamin E TPGS). Other useful vitamin derivatives include, again without limitation, Vitamin E tocopheryl polyethylene glycol succinamides, such as Vitamin E tocopheryl polyethylene glycol 1000 succinamide (Vitamin E TPGSA) wherein the ester bond between polyethylene glycol and succinic acid is replaced by an amide group.

The presently useful resuspension components are present, if at all, in the compositions in accordance with the present invention in an amount effective to facilitate suspending the particles in the present compositions, for example, during manufacture of the compositions or thereafter. The specific amount of resuspension component employed may vary over a wide range depending, for example, on the specific resuspension component being employed, the specific composition in which the resuspension component is being employed and the like factors. Suitable concentrations of the resuspension component, if any, in the present compositions are often in a range of about 0.01% to about 5%, for example, about 0.02% or about 0.05% to about 1.0% (w/v) of the composition.

The availability of minimally soluble corticosteroid components, such as triamcinolone acetonide, to intraocular tissues may be limited by the dissolution rate for these substances. Slow dissolution is both good and bad for the patient. On the one hand, after a single intravitreal injection of the present composition, the mean elimination half-life for triamcinolone acetonide is advantageously quite long, for example, about 19 days in nonvitrectonized patients and measurable drug levels are detected for up to about 3 months. On the other hand, therapeutic drug levels in the vitreous compartment of the eye may not be achieved for about 1 to about 3 days, due to the slow dissolution rate of the corticosteroid component particles.

In one embodiment of the present invention, an effective amount of a solubilizing component is provided in the composition to solubilize a minor amount, that is less than 50%, for example in a range of 1% or about 5% to about 10% or about 20% of the corticosteroid component. For example, the inclusion of a cyclodextrin component, such as β-cyclodextrin, sulfo-butylether β-cyclodextrin (SBE), other cyclodextrins and the like and mixtures thereof, at about 0.5 to about 5.0% (w/v) solubilizes about 1 to about 10% of the initial dose of triamcinolone acetonide. This presolubilized fraction provides a readily bioavailable loading dose, thereby avoiding any delay time in therapeutic effectiveness.

The use of such a solubilizing component is advantageous to provide any relatively quick release of the corticosteroid component into the eye for therapeutic effectiveness. Such solubilizing component, of course, should be ophthalmically acceptable or at least sufficiently compatible with the posterior segment of the eye into which the composition is placed to avoid undue damage to the tissue in such posterior segment.

The pharmacokinetics of the corticosteroid component, for example, triamcinolone acetonide, following intravitreal administration may involve both the rate of drug dissolution and the rate of drug efflux via the anterior route. For example, following a single intravitreal injection of a composition containing 4% (w/v) of triamcinolone acetonide, TA concentration peaks (monitored in aqueous humor) after several days at thousands of nanograms per mL. This peak ($C_{max}$) is followed by a rapid decrease lasting about 200 hours, and ends in a slow elimination phase with a half-life of about 19 days. Patients typically require repeat dosing, for example about every three months.

In one embodiment of the present invention, the compositions further contain sustained release components, for example, polymers, such as poly (D,L,-lactide) or poly(D,L-lactide co-glycolide), in amounts effective to reduce local diffusion rates and/or corticosteroid particle dissolution rates. The result is a flatter elimination rate profile with a lower $C_{max}$ and a more prolonged therapeutic window, thereby extending the time between required injections for many patients.

Any suitable, preferably conditionally acceptable, release component may be employed. Useful examples are set forth above. The sustained release component is preferably biodegradable or bioabsorbable in the eye so that no residue remains over the long term. The amount of the delayed release component included may very over a relatively wide range depending, for example, on the specific sustained release component is being employed, the specific release profile desired and the like factors. Typical amounts of delayed release components, if any, included in the present compositions are in a range of about 0.05 to 0.1 to about 0.5 or about 1 or more percent (w/v) of the composition.

The present compositions can be prepared using suitable blending/processing techniques or techniques, for example, one or more conventional blending techniques. The preparation processing should be chosen to provide the present compositions in forms which are useful for placement or injection into the posterior segments of eyes of humans or animals. In one useful embodiment a concentration corticosteroid component dispersion is made by combining the corticosteroid component with water, and the excipient (other than the viscosity inducing component) to be included in the final composition. The ingredients are mixed to disperse the corticosteroid component and then autoclaved. Alternatively, the steroid powder may be γ-irradiated before addition to the sterile carrier. The viscosity inducing component may be purchased sterile or sterilized by conventional processing, for example, by filtering a dilute solution followed by lyophylization to yield a sterile powder. The sterile viscosity inducing component is combined with water to make an aqueous concentrate. Under aseptic conditions, the concentrated corticosteroid component dispersion is mixed and added as a slurry to the viscosity inducing component concentrate. Water is added in a quantity sufficient (q.s.) to provide the desired composition and the composition is mixed until homogenous.

Methods of using the present composition are provided and are included within the scope of the present invention. In general, such methods comprise administering a composition in accordance with the present invention to a posterior segment of an eye of a human or animal, thereby obtaining a desired therapeutic effect. The administering step advantageously comprises at least one of intravitreal injecting, sub-conjunctival injecting, sub-tenon injecting, retrobulbar injecting, suprachoroidal injecting and the like. A syringe apparatus including an appropriately sized needle, for example, a 27 gauge needle or a 30 gauge needle, can be effectively used to inject the composition with the posterior segment of an eye of a human or animal.

Among the diseases/conditions which can be treated or addressed in accordance with the present invention include, without limitation, the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis and Uveitis Syndrome, Vogt-Koyanagi-Harada Syndrome.

VASCULAR DISEASES/EXUDATIVE DISEASES: Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angitis, Sickle Cell Retinopathy and other Hemoglobinopathies, Angioid Streaks, Familial Exudative Vitreoretinopathy, Eales Disease.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy.

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Retinitis Pigmentosa, Systemic Disorders with Associated Retinal Dystrophies, Congenital Stationary Night Blindness, Cone Dystrophies, Stargardt's Disease and Fundus Flavimaculatus, Best'ss Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum.

RETINAL TEARS/HOLES: Retinal Detachment, Macular Hole, Giant Retinal Tear. TUMORS: Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis and the like.

The present methods may comprise a single injection into the posterior segment of an eye or may involve repeated injections, for example over periods of time ranging from about one week or about 1 month or about 3 months to about 6 months or about 1 year or longer.

The following non-limiting Examples illustrate certain aspects of the present invention.

EXAMPLES 1 TO 4

Four compositions are as follows:

| Ingredient | Example 1 | Example 2 | Example 3 | Example 4 |
|---|---|---|---|---|
| Triamcinolone acetonide | 2% (w/v) | 2% (w/v) | 4% (w/v) | 4% (w/v) |
| Sodium Hyaluronate ($0.6 \times 10^6$ DALTONS) | 0.05% (w/v) | 0.5% (w/v) | 0.05% (w/v) | 0.5% (w/v) |
| Sodium Phosphate | 0.4% (w/v) | 0.4% (w/v) | 0.4% (w/v) | 0.4% (w/v) |
| Vitamin E-TPGS | 0.5% (w/v) | 0.5% (w/v) | 0.0 | 0.0 |
| λ-cyclodextrin | 0.5% (w/v) | 0.5% (w/v) | 0.0 | 0.0 |
| Water for Injection | q.s. | q.s. | q.s. | q.s. |
| Viscosity at shear rate 0.1/second | 20 cps | 500 cps | 20 cps | 500 cps |

Each of these compositions is prepared as follows.

A concentrated triamcinolone acetonide dispersion is made by combining triamcinolone acetonide with waters Vitamin E-TPGS and λ-cyclodextrin, if any. These ingredients are mixed to disperse the triamcinolone acetonide, and then autoclaved. The sodium hyaluronate may be purchased as a sterile powder or sterilized by filtering a dilute solution followed by lyophylization to yield a sterile powder. The sterile sodium hyaluronate is dissolved in water to make an aqueous concentrate. The concentrated triamcinolone acetonide dispersion is mixed and added as a slurry to the sodium hyaluronate concentrate. Water is added q.s. and the mixture is mixed until homogenous.

Each of these compositions produced a loose floctuation of triamcinolone acetonide that is easily re-suspended by gentle inversion. These compositions can be marketed in small volume pharmaceutical grade glass boftles, and are found to be therapeutically effective against macular edema when injected intravitreally into human eyes.

EXAMPLES 5 to 7

Three compositions are as follows:

| Ingredient | Example 5 | Example 6 | Example 7 |
|---|---|---|---|
| Triamcinolone acetonide | 2.0% (w/v) | 4.0% (w/v) | 8.0% (w/v) |
| Sodium hyaluronate | 3.0% (w/v) | 2.5% (w/v) | 2.0% (w/v) |
| Sodium Phosphate | 0.4% (w/v) | 0.4% (w/v) | 0.4% (w/v) |
| Water for Injection | q.s. | q.s. | q.s. |
| Viscosity at shear rate 0.1/second | 180,000 cps | 120,000 cps | 80,000 cps |

These compositions are prepared in a manner substantially analogous to that set forth in Example 1.

The high viscosities of the compositions substantially slows the particle sedimentation rate to an extent that no resuspension processing is necessary or required over the estimated shelf life, e.g., about 2 years, of the compositions. These compositions can be marketed in prefilled syringes since they can not easily be removed by a needle and syringe from a container. However, with the compositions in prefilled syringes, the compositions can be effectively injected into the posterior segment of an eye of a human using a 27 gauge or a 30 gauge needle to provide a desired therapeutic effect in the human eye.

The compositions of Examples 5 to 7 employ or contain a sufficient concentration of high molecular weight sodium hyaluronate so as to form a gelatinous plug or drug depot upon intravitreal injection into a human eye. Triamcinolone acetonide particles are, in effect, trapped or held within this viscous plug, so that undesirable "pluming" does not occur, and the risk of drug particles disadvantageously seftling directly on the retinal tissue is substantially reduced, for example, relative to using a composition with a water like viscosity, such as Kenalog®40. Since sodium hyaluronate solutions are subject to dramatic shear thinning, these formulations are easily injected through 27 gauge or even 30 gauge needles.

EXAMPLES 8 and 9

Two compositions are as follows:

| Ingredient | Example 8 | Example 9 |
|---|---|---|
| Triamcinolone acetonide | 2.0% (w/v) | 8.0% (w/v) |
| Sodium hyaluronate | 2.5% (w/v) | 2.3% (w/v) |
| Sodium chloride | 0.63% (w/v) | 0.6% (w/v) |
| dibasic sodium phosphate, heptahydrate | 0.30% (w/v) | 0.30% (w/v) |
| Monobasic sodium phosphate, monohydrate | 0.04% (w/v) | 0.04% (w/v) |
| Water for Injection | q.s. | q.s. |
| Viscosity at shear rate 0.1/second | 170,000 25% cps | 200,000 25% cps |

These compositions are prepared in a manner substantially analogous to that set forth in Example 1.

The high viscosities of the compositions substantially slows the particle sedimentation rate to an extent that no resuspension processing is necessary or required over the estimated shelf life, e.g., about 2 years, of the compositions. These compositions can be marketed in prefilled syringes since they can not easily be removed by a needle and syringe from a container. However, with the compositions in prefilled syringes, the compositions can be effectively injected into the posterior segment of an eye of a human using a 27 gauge or a 30 gauge needle to provide a desired therapeutic effect in the human eye.

The sodium hyaluronate powders used in these compositions (as well as in the other compositions identified in the Examples herein) have water contents in a range of about 4% to about 20%, preferably about 4% to about 8%, by weight. The water content of the powder, and in particular the variation in water contents for powder to powder, can result in variations in the viscosities of two or more compositions in accordance with the present invention which have the same "nominal" chemical make-ups. Thus, the viscosities indicated herein should be understood to be target viscosities, with the composition being acceptable for use if the actual viscosity of the composition is within plus or minus. ( ) about 25% or about 30% or about 35% of the target viscosity.

Because each of the compositions set forth in the Examples has a density of about 1 gm/ml, the percentages set forth herein as being based on weight per volume (w/v) can also be considered as being based on weight per weight (w/w).

The compositions of Examples 8 and 9 employ or contain a sufficient concentration of high molecular weight sodium hyaluronate so as to form a gelatinous plug or drug depot upon intravitreal injection into a human eye. Triamcinolone acetonide particles are, in effect, trapped or held within this viscous plug, so that undesirable "pluming" does not occur, and the risk of drug particles disadvantageously settling directly on the retinal tissue is substantially reduced, for example, relative to using a composition with a water like viscosity, such as Kenalog®40. Since sodium hyaluronate solutions are subject to dramatic shear thinning, these formulations are easily injected through 27 gauge or even 30 gauge needles.

While this invention has been described with respect to various specific examples and embodiments, it is to be understood that the invention is not limited thereto and that it can be variously practiced within the scope of the following claims.

We claim:

1. A method of treating an ocular posterior segment disorder comprising administering a composition to a posterior segment of an eye of a human or animal, the composition comprising:
   (a) about 2% to about 8% triamcinolone;
   (b) about 2.3% to about 2.5% sodium hyaluronate;
   (c) about 0.6% to about 0.63% sodium chloride
   (d) about 0.3% dibasic sodium phosphate;
   (e) about 0.04% monobasic sodium phosphate;
   (f) water, and
   (g) no added preservative,
   wherein the composition has a viscosity of about 200,000 cps at a shear rate of 0.1/second and provides a triamcinolone half life of at least 19 days after administration.

2. The method of claim 1 wherein the administering step comprises intravitreal injecting.

3. The method of claim 1 wherein the administering step comprises subconjunctival injecting.

4. The method of claim 1 wherein the administering step comprises sub-tenon injecting.

5. The method of claim 1 wherein the administering step comprises retrobulbar injecting.

6. The method of claim 1 wherein the administering step comprises suprachoroidal injecting.

7. The method of claim 1, wherein the intravitreal injection takes place through a 27 to 30 gauge needle.

8. The method of claim 1, wherein the triamcinolone is a triamcinolone acetonide.

9. A method of treating an ocular posterior segment disorder, the method comprising the step of administering a composition to a posterior segment of an eye of a human or animal, the composition comprising: (a) about 2% to about 8% triamcinolone, the triamcinolone being present in a plurality of particles that remain substantially uniformly suspended in the composition for at least 1 year without requiring resuspension processing, (b) about 2.3% to about 2.5% sodium hyaluronate; (c) about 0.6% to about 0.63% sodium chloride; (d) about 0.3% dibasic sodium phosphate; (e) about 0.04% monobasic sodium phosphate; (f) water, and (g) no added preservative, wherein the composition has a viscosity of about 200,000 cps at a shear rate of 0.1/second and provides a triamcinolone half life of at least 19 days.

10. The method of claim 9 wherein the administering step comprises intravitreal injecting.

11. The method of claim 9 wherein the administering step comprises subconjunctival injecting.

12. The method of claim 9 wherein the administering step comprises sub-tenon injecting.

13. The method of claim 9 wherein the administering step comprises retrobulbar injecting.

14. The method of claim 9 wherein the administering step comprises suprachoriodal injecting.

15. The method of claim 1 wherein said composition comprises about 8% triamcinolone.

16. The method of claim 9 wherein said composition comprises about 8% triamcinolone.

17. A method of treating an ocular posterior segment disorder comprising administering a composition to a posterior segment of an eye of a human or animal, the composition consisting essentially of:
   (a) about 8% triamcinolone;
   (b) about 2.3% sodium hyaluronate;
   (c) about 0.6% sodium chloride
   (d) about 0.3% dibasic sodium phosphate;
   (e) about 0.04% monobasic sodium phosphate;
   (f) water, and
   (g) no added preservative,
   wherein the composition has a viscosity of about 200,000 cps at a shear rate of 0.1/second and provides a triamcinolone half life of at least 19 days after administration.

18. A method of treating an ocular posterior segment disorder comprising administering a composition to a posterior segment of an eye of a human or animal, the composition consisting of:
   (a) 2% to 8% triamcinolone;
   (b) about 2.3% to about 2.5% sodium hyaluronate;
   (c) no added preservative; and
   (d) opthalmically acceptable excipients comprising about 0.6% to about 0.63% sodium chloride, about 0.3% dibasic sodium phosphate, about 0.04% monobasic sodium phosphate, and water;
   wherein the composition has a viscosity of about 200,000 cps at a shear rate of 0.1/second and provides a triamcinolone half life of at least 19 days after administration.

* * * * *